(12) United States Patent
Yang

(10) Patent No.: US 12,082,988 B2
(45) Date of Patent: Sep. 10, 2024

(54) METHOD FOR COATING DENTAL IMPLANT

(71) Applicant: Unidental Co., Ltd., Gwangmyeong-si (KR)

(72) Inventor: Sung Joon Yang, Yongin-si (KR)

(73) Assignee: UNIDENTAL CO., LTD., Gwangmyeong-si (KR)

( * ) Notice: Subject to any disclaimer, the term of this patent is extended or adjusted under 35 U.S.C. 154(b) by 167 days.

(21) Appl. No.: 17/458,220

(22) Filed: Aug. 26, 2021

(65) Prior Publication Data

US 2023/0053155 A1 Feb. 16, 2023

(30) Foreign Application Priority Data

Jul. 13, 2021 (KR) ........................ 10-2021-0091377

(51) Int. Cl.
*A61C 8/00* (2006.01)
*B05D 3/10* (2006.01)
*C09D 165/04* (2006.01)

(52) U.S. Cl.
CPC .......... *A61C 8/0013* (2013.01); *A61C 8/0016* (2013.01); *B05D 3/102* (2013.01); *C09D 165/04* (2013.01); *A61C 8/005* (2013.01)

(58) Field of Classification Search
CPC ............. B05D 3/102; B05D 3/04; B05D 1/60
See application file for complete search history.

(56) References Cited

U.S. PATENT DOCUMENTS

| 3,288,728 | A | * | 11/1966 | Gorham | ............... | C08G 61/025 570/208 |
| 2006/0029721 | A1 | * | 2/2006 | Chappa | .................... | B05D 1/60 427/255.6 |
| 2010/0150985 | A1 | * | 6/2010 | Just | ....................... | A61C 8/0013 433/81 |
| 2019/0117981 | A1 | * | 4/2019 | Bilu | ...................... | A61N 1/3752 |

FOREIGN PATENT DOCUMENTS

| KR | 10-1737358 B1 | | 6/2017 | | |
| SE | 200800812 A | * | 10/2009 | ............ | A61C 13/00 |

OTHER PUBLICATIONS

Bange. SE200800812-A. abstract. 2008 (Year: 2008).*

* cited by examiner

*Primary Examiner* — Cachet I Proctor
(74) *Attorney, Agent, or Firm* — Han's Law Office

(57) ABSTRACT

The present disclosure relates to a coating method of implant using parylene, for coating a surface of a dental implant, including a pretreating step of pretreating the implant; and a coating step of coating a surface of the pretreated implant with a coating material to form a polymer coating layer, wherein the coating material is provided as parylene.

3 Claims, 4 Drawing Sheets

[Fig. 1]
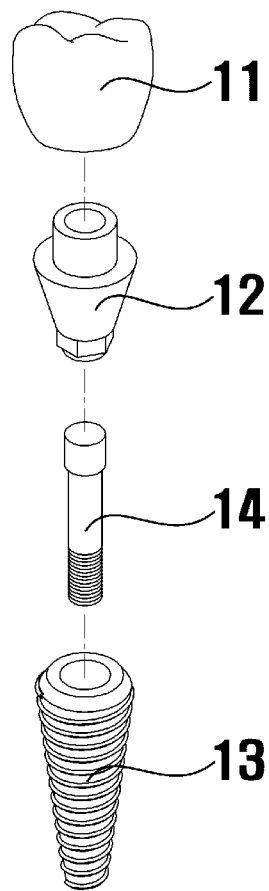
Prior Art

[Fig. 2]
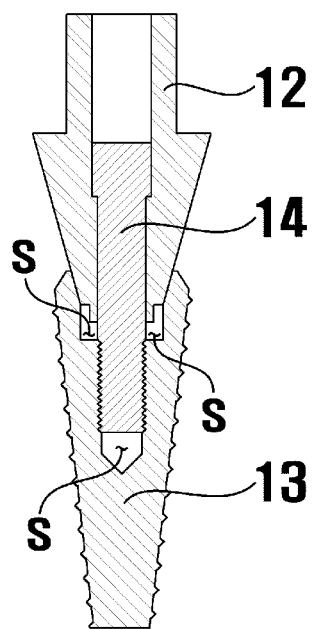
Prior Art

[Fig. 3]
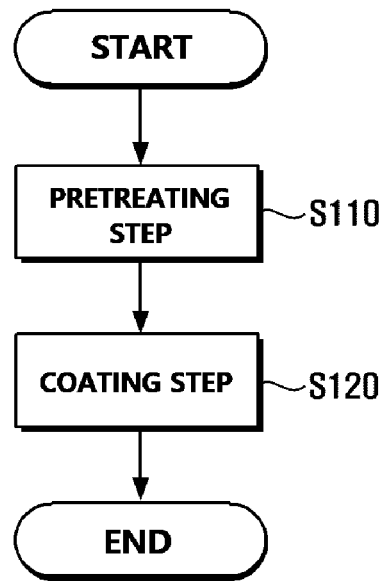
[Fig. 4]
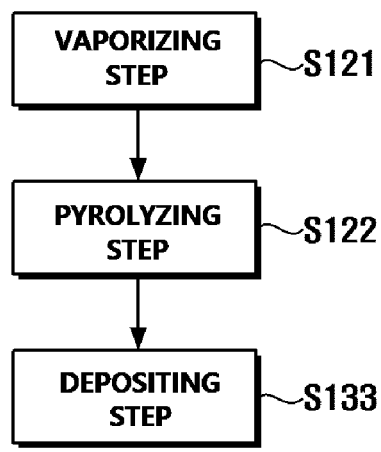

[Fig. 5]
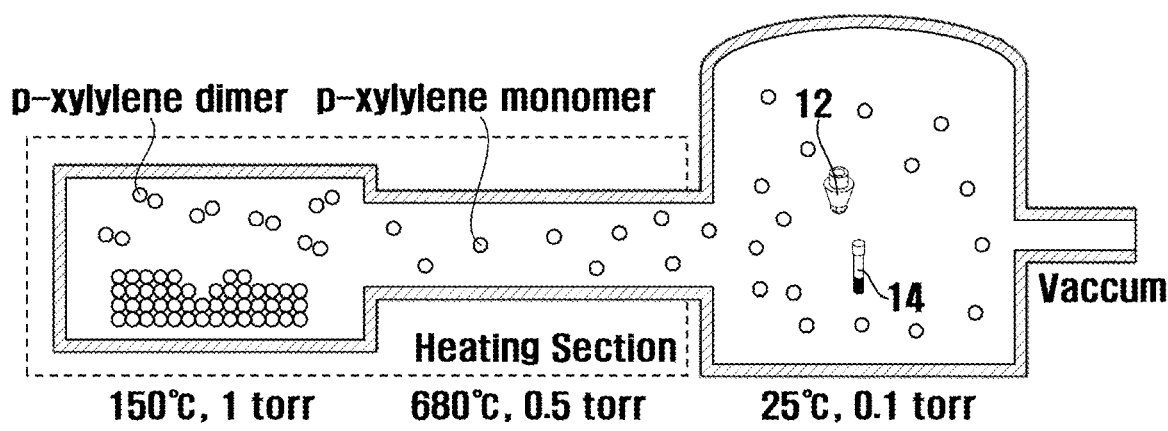

METHOD FOR COATING DENTAL IMPLANT

1. FIELD

The present disclosure relates to a coating method of implant using parylene, and more particularly, to a coating method of implant using parylene, that can uniformly coat a thin film of parylene on a surface of a dental implant, in order to effectively inhibit the growth of anaerobic bacteria.

2. BACKGROUND

A dental implant 10 is made by mechanically processing titanium or titanium alloy, and then performing various surface treatment processes such as coating to improve the intraosseous compatibility of the dental implant 10.

Such a dental implant 10 generally consists of, as illustrated in FIG. 1, a fixture 13 that is implanted in an alveolar bone, an upper structure 12 that is coupled to an upper portion of the fixture 13, a crown 11 that is formed in an artificial tooth form, and a screw 14 that is inserted inside the upper structure 12 and the fixture 13 to firmly fix the upper structure 12 and the fixture 13.

Here, the upper structure 12 is a concept that includes an abutment that, at a last stage of the dental implant 10 procedure, is finally fastened to the fixture 13, and then fastened to a lower portion of the crown 11, to support the crown 11; a cover screw that is used to prevent foreign substances from penetrating into the fixture 13 before the final abutment fastening procedure, and a healing abutment that is used to prevent gum tissue from regenerating and covering the implanted fixture 13 (that is, to maintain the shape of the gum prior to tooth extraction), and a temporary abutment that is used before the final fastening of the abutment and the crown 11.

Meanwhile, a periodontal membrane is a fibrous tissue that exists between the alveolar bone (gum bone) and cementum. It is a tissue that acts as a buffer at a time of chewing of the teeth and that protects the teeth. Especially, the periodontal membrane supplies nutrients to the alveolar bone and cementum, regenerates them, and plays an important role of eliminating various anaerobic bacteria that occur in the alveolar bone and cementum.

As illustrated in FIG. 2, the part where the fixture 13 and the upper structure 12 of the dental implant 10 are joined to each other (in particular, the part where the fixture 13 and the abutment are joined is called a fixture-abutment connection or IAJ (referred to as an implant-abutment junction) or the portion where the crown 11 and the upper structure 12 are joined to each other inevitably has a minute space (s).

In the case of a conventional dental implant 10, there is a problem because the configuration for performing the function of the above-described periodontal membrane does not exist, so various anaerobic bacteria may proliferate in the corresponding space (s), which develops into peri-implantitis and causes damage to the bone tissue, bone loss, and the like, resulting in implant failure.

SUMMARY

Therefore, a purpose of the present disclosure is to resolve the aforementioned problems of prior art, that is, to provide a coating method of implant using parylene, that can uniformly coat a thin film of parylene on a surface of a dental implant, in order to effectively inhibit the growth of anaerobic bacteria.

The aforementioned purpose is achieved by a coating method of implant using parylene, for coating a surface of a dental implant, including a pretreating step of pretreating the implant; and a coating step of coating a surface of the pretreated implant with a coating material to form a polymer coating layer, wherein the coating material is provided as parylene.

Further, the coating step may include a vaporizing step of vaporizing a cyclic para-xylylene dimer, a pyrolyzing step of pyrolyzing the vaporized cyclic para-xylylene dimer to form a para-xylylene monomer, and a depositing step of synthesizing the pyrolyzed para-xylylene monomer to the parylene and depositing the parylene on the implant in a thin film form, thereby forming a polymer coating layer.

Further, the parylene may be provided as any one of parylene-N, parylene-C, parylene-D and parylene-HT.

Further, the coating step may coat the coating material on a part where a fixture, upper structure, crown and screw of the implant are joined to each other.

Further, the coating step may coat the coating material on at least one of the upper structure and the screw of the implant.

Further, the upper structure may include a cover screw, a healing abutment, a temporary abutment and an abutment.

According to the present disclosure, a thin film of parylene can be uniformly coated on a surface of a dental implant, and by such a thin film, anaerobic bacteria can be effectively prevented from growing in a space where the fixture and the upper structure of the dental implant are joined to each other, and where the upper structure and the crown are joined to each other.

On the other hand, the effects of the present disclosure are not limited to the above-mentioned effects, and various effects may be included within the range obvious to those skilled in the art from the contents to be described below.

BRIEF DESCRIPTION OF THE DRAWINGS

FIG. 1 illustrates components of a dental implant;

FIG. 2 is a view where the components of the dental implant are combined;

FIG. 3 illustrates an entirety of steps of a coating method of implant using parylene according to an embodiment of the present disclosure;

FIG. 4 illustrates detailed steps of a coating step of the coating method of implant using parylene according to an embodiment of the present disclosure; and FIG. 5 illustrates a process where an upper structure and a screw of an implant are being coated through the coating step of the coating method of implant using parylene according to an embodiment of the present disclosure.

DETAILED DESCRIPTION

Hereinbelow, some embodiments of the present disclosure will be described in detail through the exemplary drawings. In adding reference numerals to components of each drawing, it should be noted that even if the components are displayed on different drawings, like reference numerals are used for like components as much as possible.

Further, in describing the embodiments of the present disclosure, if it is determined that a specific description of a related well-known configuration or a function interrupts the understanding of the embodiments of the present disclosure, detailed description thereof will be omitted.

Further, in describing the components of the present disclosure, terms such as a first, a second, A, B, (a), (b) and the like may be used. Such terms are merely used to distinguish those components from other components, and such terms do not limit the nature, sequence or order of the corresponding components.

Hereinbelow, a coating method of implant using parylene (S100) according to an embodiment of the present disclosure will be described in detail with reference to the accompanying drawings.

FIG. 3 illustrates an entirety of steps of a coating method of implant using parylene according to an embodiment of the present disclosure; FIG. 4 illustrates detailed steps of a coating step of the coating method of implant using parylene according to an embodiment of the present disclosure; and FIG. 5 illustrates a process where an upper structure and a screw of an implant are being coated through the coating step of the coating method of implant using parylene according to an embodiment of the present disclosure.

In the present disclosure, an implant refers to a dental implant 10 made of titanium or titanium alloy, and the present disclosure relates to an implant coating method of coating a surface of the implant, and as illustrated in FIGS. 3 to 5, a coating method of implant using parylene (S100) according to an embodiment of the present disclosure may include a pretreating step (S110) and a coating step (S120).

The pretreating step (S110) is a step of pretreatment by preparing and cleaning a base material. It is a step of cleaning and pretreating before coating a coating material on the surface of the upper structure 12 or the screw 14 of the implant.

Here, the upper structure 12 includes an abutment that, at a last stage of the dental implant 10 procedure, is finally fastened to a fixture 13, and then fastened to a lower portion of a crown 11, to support the crown 11; a cover screw that is used to prevent foreign substances from penetrating into the fixture 13 before the final abutment fastening procedure, a healing abutment that is used to prevent gum tissue from regenerating and covering the implanted fixture 13 (that is, to maintain the shape of the gum before tooth extraction), and a temporary abutment that is used before the final fastening of the abutment and the crown 11.

Meanwhile, the pretreating step (S110) may perform pretreatment by roughening the surface in order to improve the biocompatibility of the fixture 13. Here, various pretreatment methods known in the related art may be used. For example, for the pretreating step (S110), the Sandblast Large grit Acid etch (SLA) surface treatment method which involves blasting particles of metal such as aluminum and shaving a main body of the fixture 13 and then acid corroding the same, the Titanium Plasma Sprayed surface (TPS) surface treatment method which is also called the high-temperature spraying method, in which the main body of the fixture 13 is shaved by machinery and then a different titanium is melted at a high temperature and sprayed so that it can be attached to the surface of the implant, and the Resorbable Blast Media (RBM) surface treatment method which involves treating the surface using absorbent particles such as calcium phosphate may be used.

The coating step (S120) is a step of coating a coating material on the pretreated surface of the implant to form a coating layer, and in the present disclosure, parylene (poly (para-xylylene)) may be used.

In order to improve the corrosion resistance and abrasion resistance of implants and to inhibit bacterial growth, techniques for coating various materials on the surface have been researched and developed. However, existing materials cannot be evenly deposited on the surface of an implant, resulting in pin-holes and voids in the coating layer, and the thickness of the coating layer is not uniform either, thus there was a problem that the target corrosion resistance and abrasion resistance could not be achieved, and the effect of inhibiting the bacterial growth was low.

Parylene is composed of a group of polymers capable of vapor deposition, and its name is given according to the substituent, and it can be uniformly coated on any base material regardless of its shape, and can be densely coated in deep holes or cracks. Especially, parylene has an advantage that it does not give thermal stress to the base material during the coating process, and that adjusting the thickness of the coating is easy. Such parylene may be formed as a continuous thin film having a thin structure ranging from several hundred nanometers to one hundred micrometers by vapor deposition and then deposited on the base material.

Further, parylene has excellent biocompatibility and is stable biochemically, and thus is harmless to the human body, and a parylene coating layer is known to be effective in inhibiting anaerobic bacteria.

Accordingly, by coating the aforementioned parylene on the pretreated surface of the implant, the coating step (S120) of the present disclosure can improve the biocompatibility, corrosion resistance and abrasion resistance of the implant, and effectively inhibit the growth of anaerobic bacteria as well.

Here, parylene of the present disclosure may be provided as one of parylene-N, parylene-C, parylene-D, and parylene-HT.

The chemical formula of parylene-N is the same as Chemical Formula 1 below, and the formation process of parylene-N is as in Chemical Formula 2 below: cyclic para-xylylene dimer is pyrolyzed to para-xylylene monomer, and then, when being deposited on the surface of the base material, it is synthesized to poly(para-xylylene), that is parylene-N, and deposited evenly on the surface of the base material in a thin film form. This parylene-N is the most commonly used parylene, and along with the aforementioned basic features, it has a relatively small molecular size and light weight, and thus it is known to have excellent penetrability, low dielectric constant and high resistance.

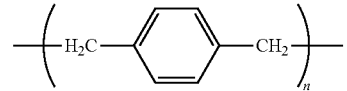

[Chemical Formula 1]

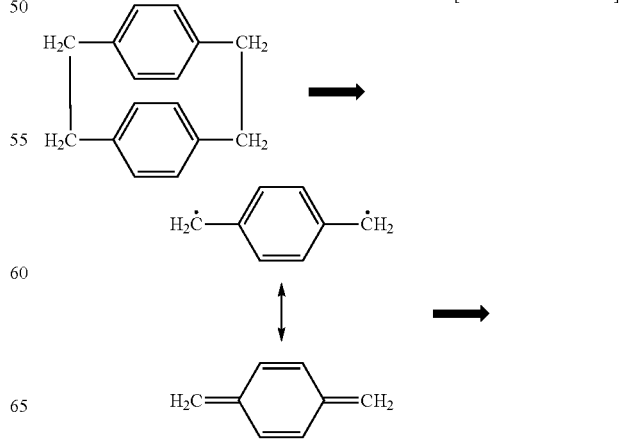

[Chemical Formula 2]

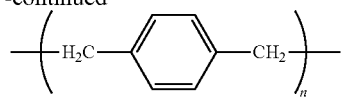

Parylene-C is a kind of chlorinated parylenes, in which one of the hydrogens of the aryl ring is substituted with chlorine (Cl), and the chemical formula of parylene-C is the same as Chemical Formula 3 below, and the formation process of parylene-C is the same as the formation process of parylene-N as in Chemical Formula 4 below. Such parylene-C is known to have excellent moisture-proof properties, relatively high dielectric strength, and high deposition power, along with the aforementioned basic characteristics of parylene.

[Chemical Formula 3]

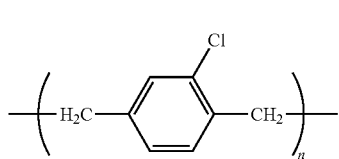

[Chemical Formula 4]

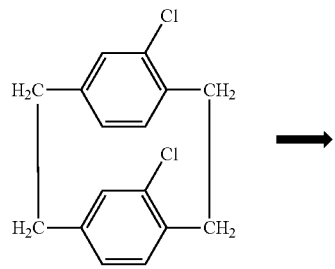

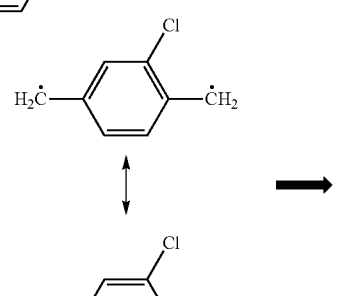

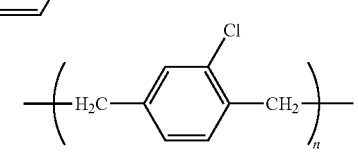

Parylene-D is a kind of chlorinated parylenes in which two hydrogens of the aryl ring are substituted to chlorine (Cl), and the chemical formula of parylene-D is the same as Chemical Formula 5 below, and the formation process of parylene-D is the same as the formation process of parylene-N as in Chemical Formula 6 below. Besides the aforementioned basic characteristics of parylene, this parylene-D has a relatively large molecular size compared to other parylenes, and thus it has lower activity and penetration power, but gives physical rigidity to the coating layer, and excellent heat resistance and chemical resistance. Further, parylene-D has a good yield compared to other parylenes.

[Chemical Formula 5]

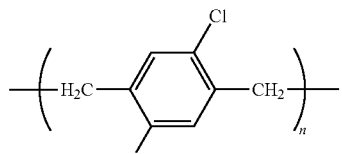

[Chemical Formula 6]

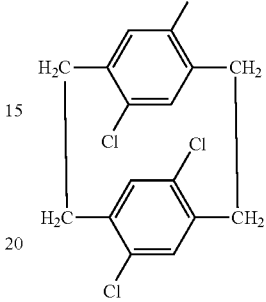

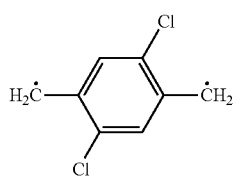

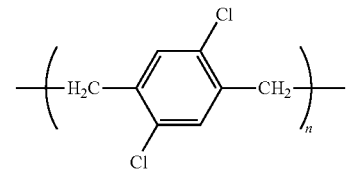

Parylene-HT is a kind of fluorinated parylenes in which four hydrogens of an aliphatic chain are substituted to fluorine (F), and the chemical formula of parylene-HT is as Chemical Formula 7 below, and the formation process of parylene-HT is the same as the formation process of parylene-N as in Chemical Formula 8 below. Such parylene-HT has the most excellent heat resistance, UV stability and crevice penetration among parylenes, and parylene-HT is known to have the lowest friction coefficient and dielectric constant among parylenes.

[Chemical Formula 7]

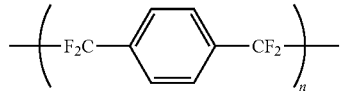

-continued

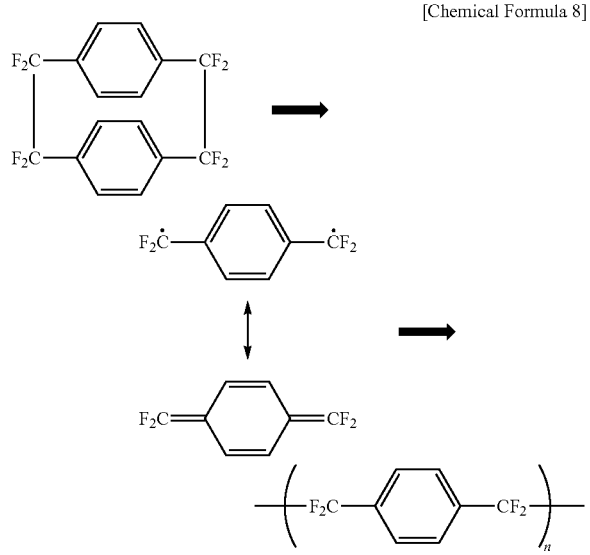
[Chemical Formula 8]

Further, as illustrated in FIGS. 4 and 5, in more detail, the coating step (S120) includes a vaporizing step (S121), a pyrolyzing step (S122), and a depositing step (S123).

The vaporizing step (S121) is a step of vaporizing a cyclic para-xylylene dimer at a high temperature (vaporization). It is a step in which a raw material in powder form, that is, the cyclic para-xylylene dimer, is charged into a vaporization chamber, and then heated to form a dimer gas. It is preferable that the vaporization at this vaporizing step (S121) be carried out at a temperature between 120° C. to 300° C. and under a pressure of 100 torr. If the temperature is lower than the aforementioned temperature, there is a problem that the vaporization of the dimer will not be carried out properly, and if the temperature is higher than the aforementioned temperature, there is a problem that before being deposited on an implant at the depositing step (S123) that will be described hereinbelow, a monomer will be formed and synthesized to parylene, which prevents the implant from being coated properly.

The pyrolyzing step (S122) is a step of pyrolyzing the vaporized cyclic para-xylylene dimer at a high temperature to form a para-xylylene monomer (that is, forming a monomer from a dimer). It is a step in which the dimer gas that has been formed at the vaporizing step (S121) and then transferred to the pyrolyzing chamber, is heated at a high temperature, and the cyclic para-xylylene dimer is pyrolyzed to a highly reactive para-xylylene monomer, and then a monomer gas is formed. It is desirable that the pyrolysis at such a pyrolyzing step (S122) is carried out at a temperature between 600° C. and 850° C., and under an appropriate vacuum pressure, and if the temperature is lower than the aforementioned temperature, there is a problem that the cyclic para-xylylene dimer is not sufficiently pyrolyzed, and if the temperature is higher than the aforementioned temperature, there is a problem that the dimer or monomer may be transformed.

The depositing step (S123) is a step of forming a coating layer by synthesizing the pyrolyzed para-xylylene monomer to parylene at a low temperature, and depositing the parylene on the implant in a thin film form. It is a step in which the monomer gas formed at the pyrolyzing step (S122) and transferred to a depositing chamber, forms a thin and transparent parylene thin film on all surfaces inside the depositing chamber at room temperature. It is preferable that such a depositing step (S123) is carried out at room temperature (RT), preferably at a temperature of 25° C., and under a pressure that is not more than 100 MT. If the depositing step is carried out outside the aforementioned temperature and pressure, there is a problem that the parylene thin film cannot be properly formed on the surface of the implant.

Meanwhile, it is preferable that the parylene being coated on the implant at the depositing step (S123) is coated to have a thickness of 100 nm~50 um.

If the thickness of coated parylene is not more than 100 nm, that is, if it is too thin, parylene is not be sufficiently coated on the area of the implant to be coated, which may make it difficult to properly exhibit the anaerobic bacteria suppression function, and if the thickness of the coated parylene is 50 um or more, that is, if it is too thick, an excessively thick coating layer will be formed, making it difficult for each of the components of the implant to combine, and when each of the components combine, the coating layer may come off.

Meanwhile, the coating step (S120) coats the aforementioned parylene on, especially, the part where the fixture 13 and the upper structure 12 of the implant are joined to each other, for example, the fixture-abutment connection or implant-abutment junction (IAJ), so that the anaerobic bacteria cannot grow on the implant. For this purpose, the coating step (S120) may coat the parylene on at least one part of the inner surface and outer surface of the upper structure 12, and the outer surface of the screw 14. Here, as aforementioned, the upper structure 12 is a concept that includes an abutment, a cover screw, a healing abutment, and a temporary abutment.

Meanwhile, the coating layer formed at the depositing step (S123) may include citric acid. That is, the depositing step (S123) may additionally coat the citric acid on the surface of the implant. In the process at the depositing step (S123) of forming the coating layer by synthesizing the pyrolyzed para-xylylene monomer to parylene, and then depositing it on the implant in a thin film form to form a coating layer, the citric acid may be dispersed inside the depositing chamber so that the citric acid is included in the coating layer. The chemical formula of the citric acid is as in Chemical Formula 9 below, and the citric acid is known to effectively inhibit the growth of anaerobic bacteria in the oral cavity, and to effectively remove elements of bad breath in the oral cavity.

[Chemical Formula 9]

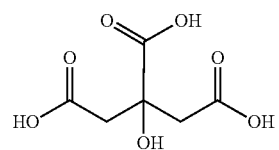

Here, it is desirable that the amount of the citric acid being coated on the implant at the depositing step (S123) is between 10 and 100 ug per unit area ($mm^2$). If the coated amount is not more than 10 ug/$mm^2$, the citric acid will not be sufficiently coated on the subject part of the implant to be coated, and thus making it difficult to properly exhibit the anaerobic bacteria suppression function, and if the coated amount is 100 ug/$mm^2$ or more, there is a problem that enamel erosion in the oral cavity may occur due to excessive citric acid.

According to the coating method of implant using parylene (S100) according to an embodiment of the present disclosure, that includes the aforementioned pretreating step (S110) and the coating step (S120), the parylene thin film may be uniformly coated on the surface of the dental implant 10, and by such a thin film, anaerobic bacteria can be effectively prevented from growing in a space where the fixture 13 and the upper structure 12 of the dental implant 10 are joined to each other, and where the upper structure 12 and the crown 11 are joined to each other.

Through the specific examples of the present disclosure described hereinbelow, functions and effects of the present disclosure will be described in detail. However, these are merely to exemplify the present disclosure, and not to limit the scope of right of the present disclosure in any way.

Example 1—Dental Implant where Parylene Coating Layer is Formed after Pretreatment The fixture 13 of the dental implant 10 was pretreated and prepared using the SLA surface treatment method, and the upper structure 12 and the screw 14 of the dental implant 10 were each cleaned and pretreated, and then the pretreated upper structure 12 and screw 14 were transferred to the depositing chamber of the parylene coating device, to form a parylene-C coating layer, respectively. The parylene coating was performed using the PDS 2060PC device of the Specialty Coating Systems (SCS), and the parylene-C was set to be coated in a thickness of about 100 nm on each of the upper structure 12 and the screw 14. Thereafter, the fixture 13, the upper structure 12 and the screw 14 were combined with each other.

Example 2—Dental Implant where Parylene and Citric Acid Coating Layer is Formed after Pretreatment The fixture 13 of the dental implant 10 was pretreated and prepared using the SLA surface treatment method, and the upper structure 12 and the screw 14 of the dental implant 10 were each cleaned and pretreated, and then the pretreated upper structure 12 and screw 14 were transferred to the depositing chamber of the parylene coating device, to form a parylene-C coating layer that includes citric acid. The parylene coating was performed using the PDS 2060PC device of the Specialty Coating Systems (SCS), and the parylene-C was set to be coated in a thickness of about 100 nm on each of the upper structure 12 and the screw 14, and the citric acid was set to be coated in an amount of about ug/mm$^2$ respectively. Thereafter, the fixture 13, the upper structure 12 and the screw 14 were combined with each other.

Comparative Example—Pretreated Dental Implant

The fixture 13 of the dental implant 10 was pretreated and prepared using the SLA surface treatment method, and the upper structure 12 and the screw 14 were each cleaned and pretreated, but after that, an additional coating process was not performed on the upper structure 12 and the screw 14. Thereafter, the fixture 13, the upper structure 12 and the screw 14 were combined with each other.

Test Example—Bacterial Growth Inhibiting Power Test 1

In order to identify the bacterial growth inhibiting power of the dental implant on which the parylene and citric acid coating layer is formed, a test was carried out as below. In a liquid medium made by putting a nutrient medium into distilled water, a small amount of *Prevotella intermedia*, which is a representative periodontal causative bacterium and anaerobic bacterium, was put in as a platinum tip, and then cultured for 24 hours. After that, strain solution was diluted to 1/100,000 and placed in a vial containing the dental implant of Example 1, the dental implant of Example 2, and the dental implant of the Comparative Example, respectively, and cultured for 24 hours. A small amount of the solution from the vial was spread on a solid medium of the culture dish, and after standing for 24 hours, the proliferation degree of *Prevotella intermedia* was checked.

TABLE 1

|  | Example 1 | Example 2 | Comparative Example |
| --- | --- | --- | --- |
| Prevotella intermedia (log cfu/cm$^2$) | 3.1 | 2.6 | 3.4 |

As illustrated in Table 1 above, it is shown that the dental implant of Example 1 has some effect in inhibiting the growth of anaerobic bacteria when compared to the dental implant of the comparative example, and it is shown that the dental implant of Example 2 has a significant effect in inhibiting the growth of anaerobic bacteria.

Test Example—Bacterial Growth Inhibiting Power Test 2

In a different test, *Prevotella intermedia* strain was inoculated into each of the dental implant of Example 1, the dental implant of Example 2, and the dental implant of the Comparative Example in cell number of 2×10$^6$, respectively, and cultured at 38° C. for 12 hours, and then dyed in crystal violet, and evaluated whether there is biofilm and the degree of biofilm formed due to the strain.

TABLE 2

|  | Example 1 | Example 2 | Comparative Example |
| --- | --- | --- | --- |
| Existence and degree of biofilm | Small amount | Barely occurred | Numerous occurred |

As illustrated in Table 2 above, in the case of the dental implant of the Comparative Example, numerous biofilms occurred, but in the case of the dental implant of Example 1, some biofilms occurred, but when compared to the Comparative Example, *Prevotella intermedia* showed a significant decrease. In the case of the dental implant of Example 2, when compared to Example 1 and the Comparative Example, a significantly small amount of biofilms occurred.

Hereinabove, even if all components constituting an embodiment of the present disclosure are described as being combined into one or operating in combination, the present disclosure is not necessarily limited to this embodiment. That is, as long as it is within the scope of the object of the present disclosure, one or more of all those components may be selectively combined and operated.

Further, terms such as "include", "constitute/consist of" or "has/have" and the like disclosed hereinabove mean that corresponding components may be present unless specifically stated otherwise, and thus it should be interpreted as being not excluding other components but able to contain other components. All terms, including technical or scientific terms, have the same meaning as commonly understood by one of ordinary skill in the art, unless otherwise defined. Terms generally used, such as terms defined in the dictionary, should be interpreted as being consistent with the meaning of the context of the related technology, and are not interpreted as ideal or excessively formal meanings unless explicitly defined in the present disclosure.

Further, the above description is merely illustrative of the technical idea of the present disclosure, and various modifications and variations may be made by those of ordinary skill in the technical field to which the present disclosure pertains, without departing from the essential characteristics of the present disclosure.

Therefore, the embodiments disclosed in the present disclosure are not intended to limit the technical idea of the present disclosure, but to describe it, and the scope of the technical idea of the present disclosure is not limited by these embodiments. The scope of protection of the present disclosure should be interpreted by the following claims, and all technical ideas within the scope equivalent thereto should be construed as being included in the scope of the present disclosure.

What is claimed is:

1. A method for coating a surface of a dental implant using parylene, comprising:
   pretreating the dental implant; and
   coating a surface of the pretreated dental implant with a coating material to form a polymer coating layer,
   wherein the coating comprises vaporizing a cyclic para-xylylene dimer, pyrolyzing the vaporized cyclic para-xylylene dimer to form a para-xylylene monomer, synthesizing the pyrolyzed para-xylylene monomer to the parylene and depositing the parylene on the dental implant, thereby forming the polymer coating layer,
   wherein the synthesizing comprises adding a citric acid into the pyrolyzed para-xylylene monomer,
   wherein the dental implant comprises a fixture, an upper structure coupled to an upper portion of the fixture, a screw to fix the fixture and the upper structure and a crown coupled to the upper structure,
   wherein only a surface of the upper structure and the screw are coated in order to inhibit a growth of anaerobic bacteria in a portion where at least two of the fixture, the upper structure, the screw and the crown are joined, and
   wherein a thickness of the polymer coating layer ranges from 100 nm~50 μm.

2. The method, according to claim 1,
   wherein the parylene is provided as any one of parylene-N, parylene-C, parylene-D and parylene-HT.

3. The method, according to claim 1,
   wherein the upper structure comprises a cover screw, a healing abutment, a temporary abutment and an abutment.

* * * * *